United States Patent
Seki et al.

(10) Patent No.: US 10,577,481 B2
(45) Date of Patent: Mar. 3, 2020

(54) POLYMER

(71) Applicant: CANON KABUSHIKI KAISHA, Tokyo (JP)

(72) Inventors: Masanori Seki, Yokohama (JP); Keigo Mizusawa, Tokyo (JP); Ryuji Higashi, Kawasaki (JP); Masaru Sugita, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 15/951,387

(22) Filed: Apr. 12, 2018

(65) Prior Publication Data

US 2018/0305522 A1 Oct. 25, 2018

(30) Foreign Application Priority Data

Apr. 19, 2017 (JP) .................................. 2017-083067

(51) Int. Cl.
| | |
|---|---|
| C08K 5/357 | (2006.01) |
| C08L 33/02 | (2006.01) |
| C07H 19/173 | (2006.01) |
| C08K 5/3462 | (2006.01) |
| C08K 5/1535 | (2006.01) |

(52) U.S. Cl.
CPC ............ C08K 5/357 (2013.01); C07H 19/173 (2013.01); C08K 5/1535 (2013.01); C08K 5/3462 (2013.01); C08L 33/02 (2013.01); C08L 2203/02 (2013.01)

(58) Field of Classification Search
CPC .... C08K 5/357; C08K 5/3462; C08K 5/1535; C07H 19/173; C08L 33/02; C08L 2203/02
See application file for complete search history.

(56) References Cited

U.S. PATENT DOCUMENTS

| | | | | |
|---|---|---|---|---|
| 4,434,150 | A | * | 2/1984 | Azad .................... G01N 33/532 252/645 |
| 6,007,992 | A | * | 12/1999 | Lin ......................... C07H 19/06 435/6.12 |
| 9,298,118 | B2 | | 3/2016 | Kawamura et al. |
| 9,593,243 | B2 | | 3/2017 | Tsujii et al. |
| 9,618,867 | B2 | | 4/2017 | Toyoda et al. |
| 2014/0057357 | A1 | | 2/2014 | Sasaki et al. |

FOREIGN PATENT DOCUMENTS

| | | |
|---|---|---|
| WO | 99/024452 A2 | 5/1999 |
| WO | 2006/029023 A2 | 3/2006 |
| WO | 2012/077800 A1 | 6/2012 |
| WO | 2012/133306 A1 | 10/2012 |

OTHER PUBLICATIONS

Tani et al., U.S. Appl. No. 15/993,947, filed May 31, 2018.
Zhichun Li et. al., "Synthesis of New Derivatives of 8-oxoG-Clamp for Better Understanding the Recognition Mode and Improvement of Selective Affinity," Bioorg. 18 Med. Chem. 3992-3998 (Apr. 2010).
Kuei-Ping Lin et. al., "A Cytosine Analogue Capable of Clamp-Like Binding to a Guanine in Helical Nucleic Acids," 120 (33) J. Am. Chem. Soc. 8531-8532 (Aug. 1998).

* cited by examiner

*Primary Examiner* — Robert S Jones
(74) *Attorney, Agent, or Firm* — Venable LLP

(57) ABSTRACT

Provided is a polymer that can detect a low-molecular weight compound, in particular, 8-OHdG with high sensitivity and can be repeatedly used. Specifically, provided is a polymer including repeating units each represented by the following formula (1). In the formula (1), $R^1$ and $R^2$ are each independent for each repeating unit, $R^1$ represents a hydrogen atom or an alkyl group, and $R^2$ represents a group represented by the following formula (2) in at least one repeating unit, and represents a phenyl group, a hydroxyl group, an amino group, or a carboxyl group in any other repeating unit, and the group may be substituted with an alkyl group. In the formula (2), $R^3$ represents a hydrogen atom, an alkyl group, or an aryl group, L represents a divalent linking group, and * represents a site to be bonded to the carbon atom bonding to $R^1$ in formula (1).

8 Claims, No Drawings

POLYMER

BACKGROUND OF THE INVENTION

Field of the Invention

The present invention relates to a novel polymer including a phenoxazine compound structure.

Description of the Related Art

The 8-position of deoxyguanosine serving as one base forming DNA is oxidized by an oxidizing action exhibited by active oxygen to produce 8-oxo-2'-deoxyguanosine (hereinafter described as "8-OHdG"). 8-OHdG thus produced is immediately excreted as a relatively stable substance in urine. Accordingly, the excretion amount of 8-OHdG is considered to reflect an influence of an active oxygen species on a living organism, and hence 8-OHdG is one of the oxidative stress markers that have been most widely used at present.

8-OHdG has such tautomers as represented below.

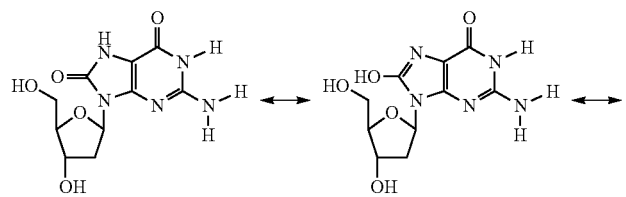

A phenoxazine compound shows an affinity for a nucleobase. Various improvements have been made to the structure of the phenoxazine compound for improving the affinity (International Publication No. WO99/024452, Patent Literature 1), and some phenoxazine compounds have each been found to have an affinity for 8-OHdG (Li, Z., et. al.; Bioorg. Med. Chem., 18, 3992-3998 (2010), Non Patent Literature 1). In addition, there is a disclosure of a phenoxazine compound fixed to silica gel particles (International Publication No. WO2012/133306, Patent Literature 2).

It takes time and labor to synthesize the phenoxazine compounds each having an affinity for 8-OHdG described in Non Patent Literature 1. In addition, any such compound has a low molecular weight, and hence it is difficult to separate the compound from 8-OHdG and a used derivative is hardly reused. In addition, the phenoxazine compound fixed to the silica gel particles described in Patent Literature 2 contains the silica gel particles as a main component, and hence the amount of the compound that can be fixed is limited, and when the compound is used in the same amount as that before the fixing, the concentration range of 8-OHdG that can be adsorbed is narrow.

An object of the present invention is to provide a polymer that has a high affinity for 8-OHdG, can be repeatedly used, and has a wide applicable concentration range.

SUMMARY OF THE INVENTION

The above-mentioned object is achieved by the present invention described below. That is, according to one embodiment of the present invention, there is provided a polymer, including repeating units each represented by the following formula (1):

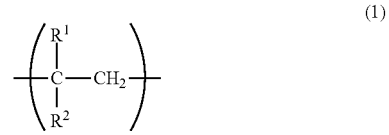

where, in the formula (1), $R^1$ and $R^2$ are each independent for each repeating unit, $R^1$ represents a hydrogen atom or an alkyl group, and $R^2$ represents a group represented by the following formula (2) in at least one repeating unit, and represents a phenyl group, a hydroxyl group, an amino group, or a carboxyl group in any other repeating unit, and the group may be substituted with an alkyl group:

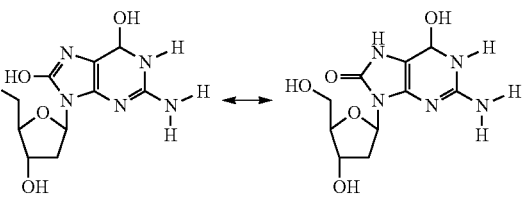

where, in the formula (2), $R^3$ represents a hydrogen atom, an alkyl group, or an aryl group, L represents a divalent linking group, and * represents a site to be bonded to the carbon atom bonding to $R^1$ in formula (1).

Further features of the present invention will become apparent from the following description of exemplary embodiments.

DESCRIPTION OF THE EMBODIMENTS

Preferred embodiments of the present invention will now be described in detail.

A polymer according to an embodiment of the present invention has a structure in which the main chain of an organic polymer and a side chain having a phenoxazine skeleton are bonded to each other. Specifically, the polymer includes repeating units each represented by the following formula (1):

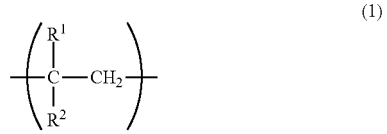

where, in the formula (1), $R^1$ and $R^2$ are each independent for each repeating unit, $R^1$ represents a hydrogen atom or an alkyl group, and $R^2$ represents a group represented by the following formula (2) in at least one repeating unit, and represents a phenyl group, a hydroxyl group, an amino group, or a carboxyl group in any other repeating unit, and the group may be substituted with an alkyl group.

The formula (2) has the structure of a phenoxazine compound:

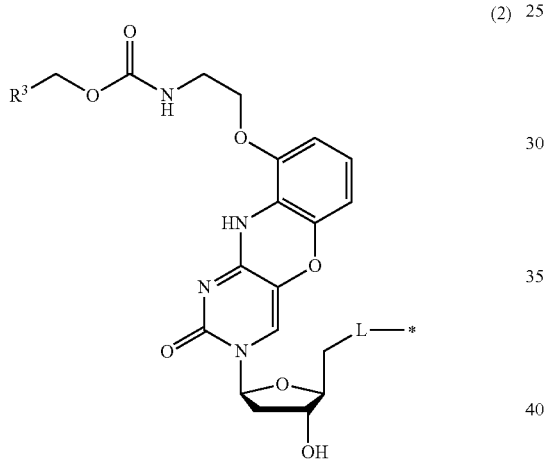

where, in the formula (2), $R^3$ represents a hydrogen atom, an alkyl group, or an aryl group, L represents a divalent linking group, and * represents a site to be bonded to the carbon atom bonding to $R^1$ in formula (1).

The alkyl group in $R^3$ in the formula (2) is not particularly limited, and examples thereof include linear, branched, and cyclic alkyl groups, such as a methyl group, an ethyl group, a n-propyl group, a n-butyl group, a n-pentyl group, a n-hexyl group, an isopropyl group, an isobutyl group, a sec-butyl group, a tert-butyl group, and a cyclohexyl group. The alkyl group may further have a substituent, such as an aryl group.

Examples of the aryl group in $R^3$ in the formula (2) include a phenyl group, a naphthyl group, an anthracenyl group, a pyrenyl group, a fluorenyl group, a fluoranthenyl group, an alkyl phenyl group, an alkyl naphthyl group, an alkyl anthracenyl group, an alkyl pyrenyl group, an alkyl fluorenyl group, and an alkyl fluoranthenyl group. Those aryl groups may each have a substituent.

The phenoxazine compound according to the embodiment of the present invention is bonded to a high-molecular weight compound having the units each represented by the formula (1) through the divalent linking group L in the formula (2). Although the linking group L is not particularly limited as long as the linking group is a divalent linking group, from the viewpoint of the ease of production of the polymer, a linking group including an amide bond or an ester bond is preferred, and a linking group including an ester bond is particularly preferred.

That is, the linking group L may be, for example, an oxycarbonyl group (—O—CO—), a carbonyloxy group (—CO—O—), a carbonylamino group (—CO—NH—), or an aminocarbonyl group (—NH—CO—), or a group further including an alkylene group at one terminal, or each of both terminals, of any one of the groups.

Specific examples of the structure of the phenoxazine compound represented by the formula (2) may be represented by the following formulae (9') to (25') and (6'). However, the present invention is not limited thereto.

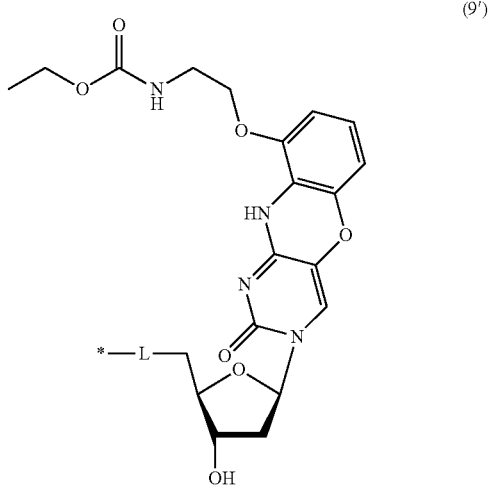

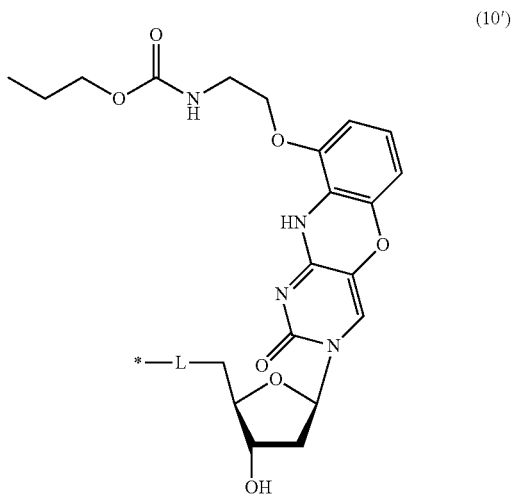

(11')
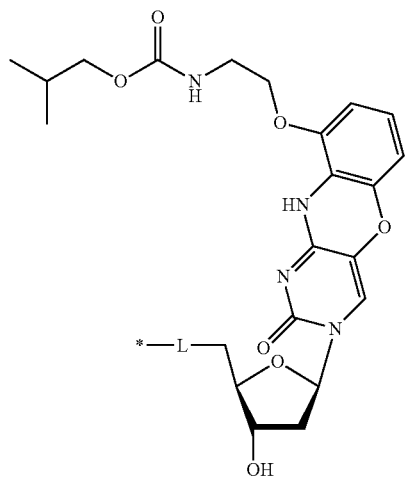
(12')
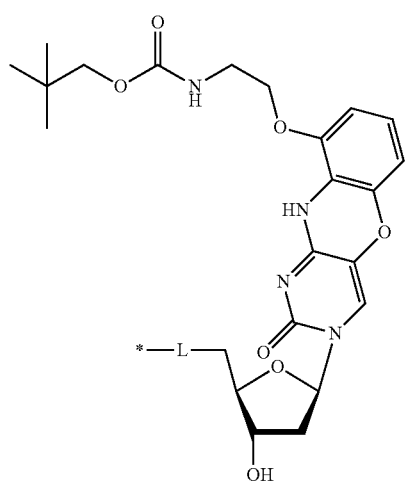
(13')
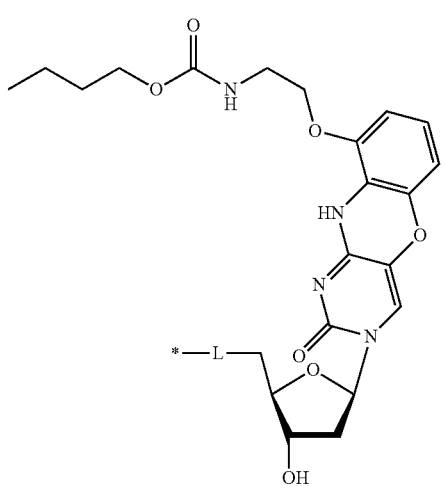
(14')
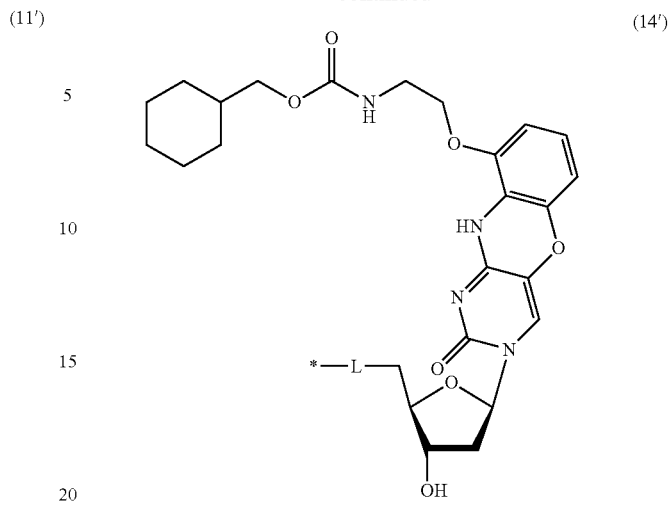
(15')
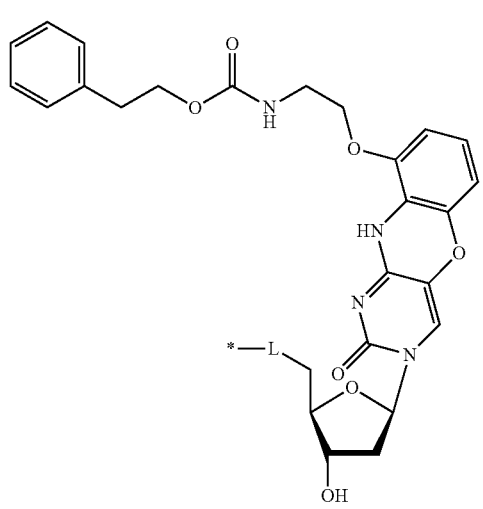
(16')
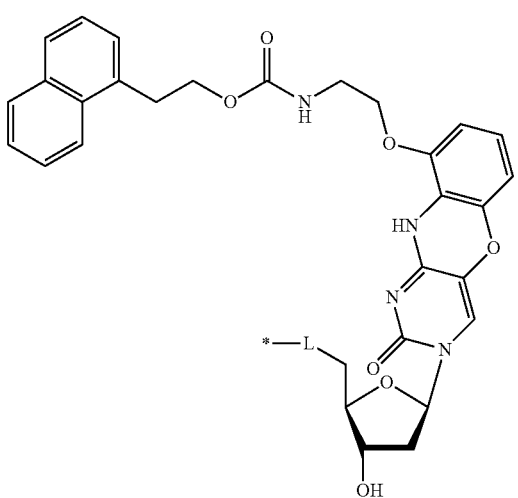

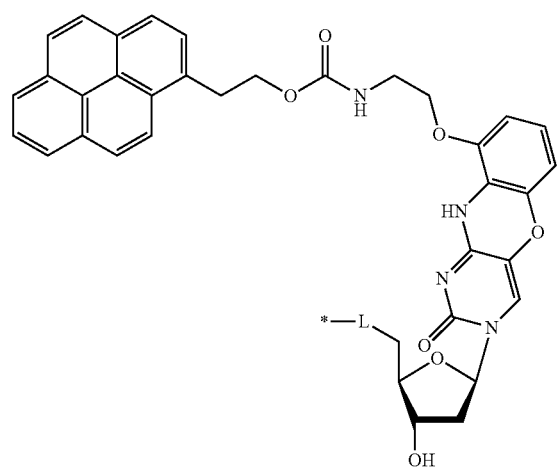
(17')
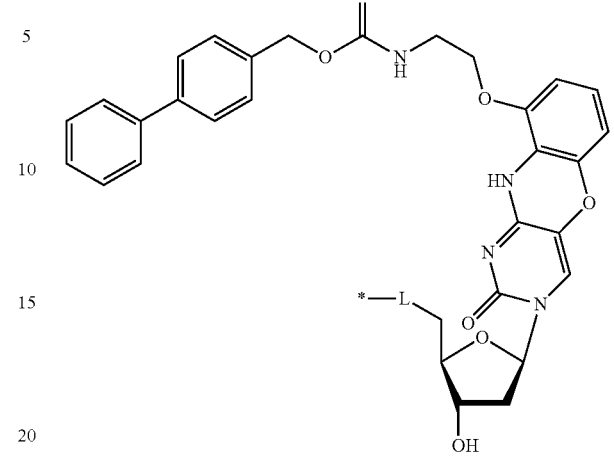
(19')
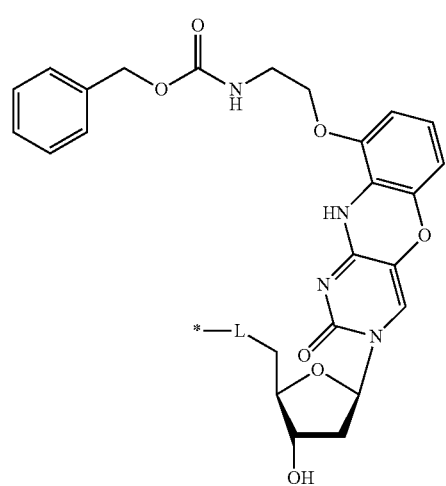
(6')
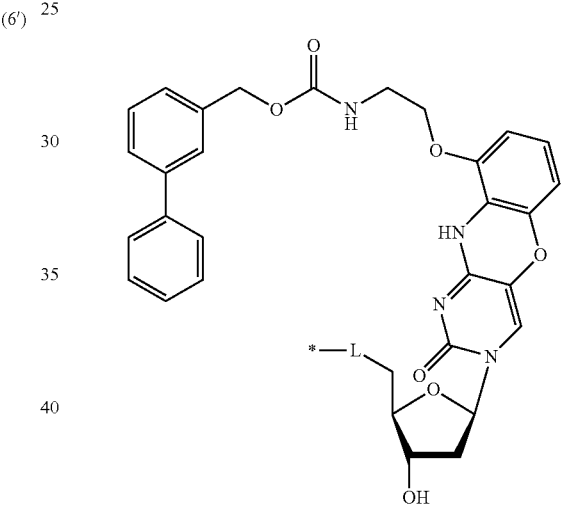
(20')
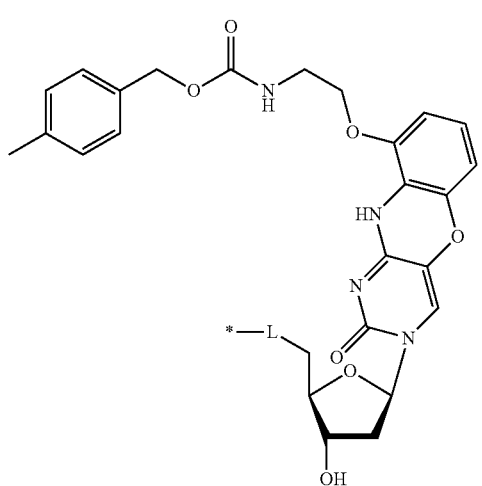
(18')
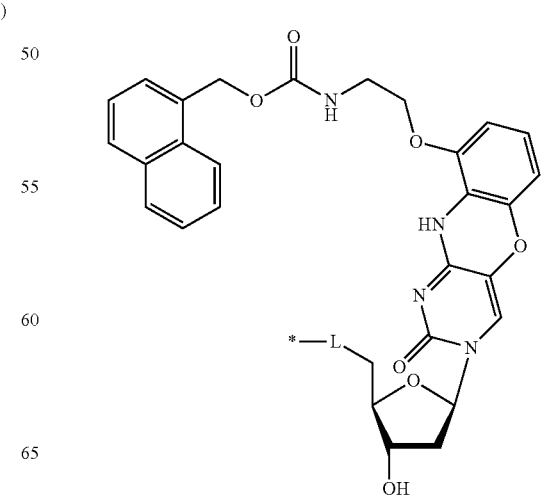
(21')

-continued (22')

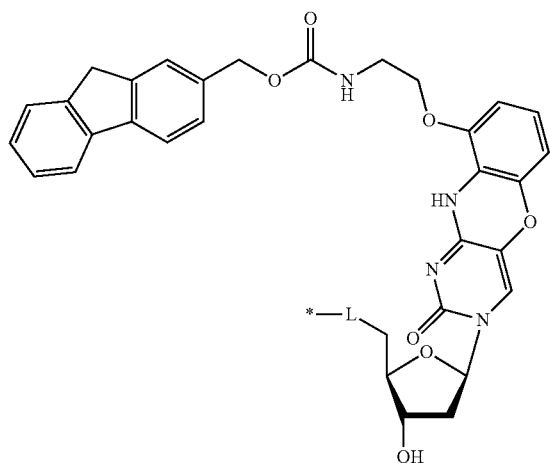

(23')

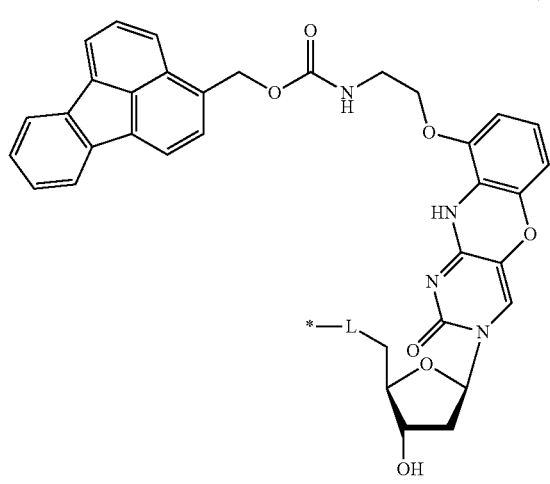

(24')

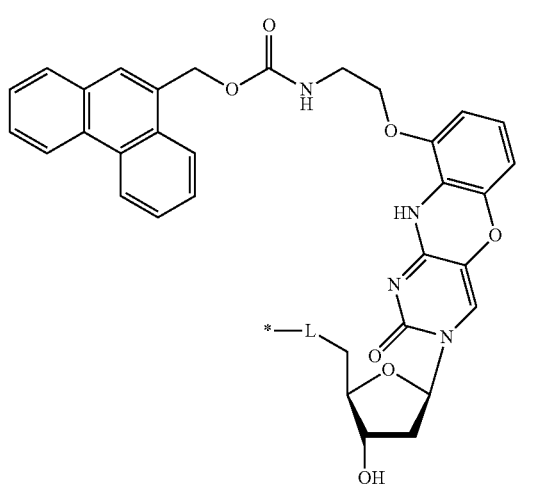

-continued (25')

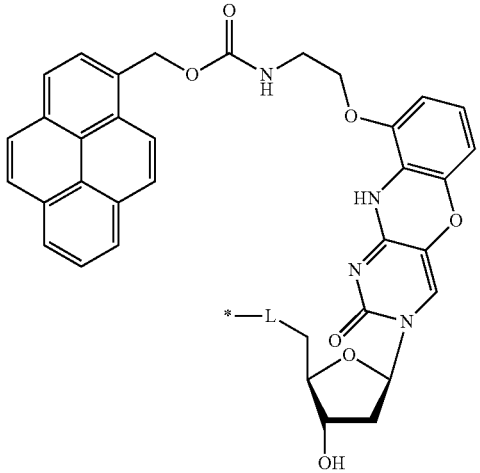

The polymer according to the embodiment of the present invention may be any one of a so-called homopolymer synthesized by the polymerization of a single monomer and a so-called copolymer synthesized by the polymerization of a plurality of monomers.

Although the alkyl group in $R^1$ in the formula (1) is not particularly limited, an alkyl group having 1 to 6 carbon atoms is preferred, and examples thereof include linear, branched, and cyclic alkyl groups, such as a methyl group, an ethyl group, a n-propyl group, a n-butyl group, a n-pentyl group, a n-hexyl group, an isopropyl group, an isobutyl group, a sec-butyl group, a tert-butyl group, and a cyclohexyl group. A case in which $R^1$ represents a hydrogen atom or a methyl group is preferred from the viewpoint of the ease of production of the polymer.

The polymer according to the embodiment of the present invention may include a plurality of structures of the phenoxazine compounds each represented by the formula (2) in itself. An increase in number of the structures of the phenoxazine compounds to be introduced can correspond even to a case in which the concentration of 8-OHdG in a solution at the time of the use of the same amount of the polymer as that before the increase is high. In addition, the polymer after the adsorption of 8-OHdG can be repeatedly used by being washed with a solvent appropriate for the composition of the polymer (e.g., methanol, ethyl acetate, or dilute hydrochloric acid).

The polymer according to the embodiment of the present invention preferably includes 30 or more and 100 or less repeating units each represented by the formula (1), and more preferably includes 40 or more and 60 or less repeating units each represented by the formula (1). When the number of the repeating units (the molecular weight of the polymer) is small, the affinity of the polymer for the solvent is high, and hence it becomes difficult to perform the separation of the polymer from 8-OHdG for repeated use of the polymer. In addition, when the number of the repeating units (the molecular weight of the polymer) is large, the affinity for the solvent reduces, and hence it becomes difficult to detect a target compound.

In addition, the polymer according to the embodiment of the present invention preferably includes 5 or more and 10 or less repeating units each represented by the formula (1) in which $R^2$ represents a group represented by the formula (2).

In addition, a polymer according to another embodiment of the present invention includes a repeating unit represented by the following formula (26):

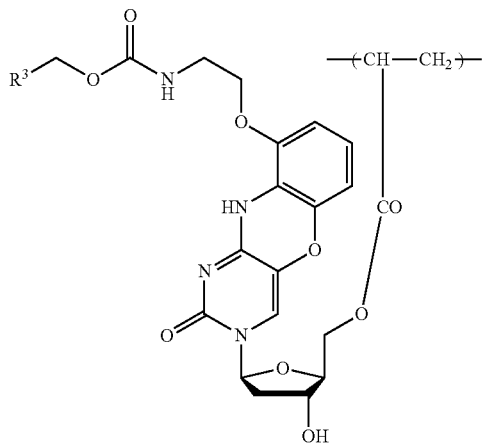

(26)

where, in the formula (26), $R^3$ represents a hydrogen atom, an alkyl group, or an aryl group. The polymer according to the embodiment of the present invention may further include a repeating unit represented by the following formula (27):

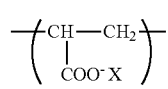

(27)

where, in the formula (27), X represents a counter ion. The counter ion is not limited, and examples thereof may include cations each derived from a hydrogen atom, a sodium atom, a potassium atom, ammonia, triethylamine, lysine, or arginine.

An example of a synthesis route for the compound according to the embodiment of the present invention is described.

The synthesis of the polymer having the monomer units each represented by the formula (1) is described. A known synthesis method may be used. Specifically, acrylic acid, methacrylic acid, an alkyl acrylate, an alkyl methacrylate, a styrene-based monomer, or the like may be used as a monomer, and may be polymerized by a method such as radical polymerization, cationic polymerization, or anionic polymerization. Of those, radical polymerization is preferred in terms of the ease of production of the polymer. In addition, a commercial product may be used as the polymer before the introduction of the structure of the phenoxazine compound. For example, a polyacrylic acid, a polymethacrylic acid, or any other acrylic resin, or JONCRYL (trademark) serving as a copolymer may be used as the commercial product. JONCRYL is a copolymer formed of (meth) acrylic acid and an alkyl methacrylate and/or a styrene-based monomer, such as α-methylstyrene, and is more specifically, for example, JONCRYL 67 (weight-average molecular weight: 12,500, acid value: 213 mgKOH/g), JONCRYL 678 (weight-average molecular weight: 8,500, acid value: 215 mgKOH/g), JONCRYL 586 (weight-average molecular weight: 4,600, acid value: 108 mgKOH/g), JONCRYL 680 (weight-average molecular weight: 4,900, acid value: 215 mgKOH/g), JONCRYL 682 (weight-average molecular weight: 1,700, acid value: 238 mgKOH/g), JONCRYL 683 (weight-average molecular weight: 8,000, acid value: 160 mgKOH/g), JONCRYL 690 (weight-average molecular weight: 16,500, acid value: 240 mgKOH/g), JONCRYL 819 (weight-average molecular weight: 14,500, acid value: 75 mgKOH/g), JONCRYL JDX-C3000 (weight-average molecular weight: 10,000, acid value: 85 mgKOH/g), or JONCRYL JDX-C3080 (weight-average molecular weight: 14,000, acid value: 230 mgKOH/g).

The structure of the phenoxazine compound may be introduced at the stage of the monomer, or may be introduced after the polymerization.

A derivative of the phenoxazine compound may be synthesized with reference to Kuei-Ying Lin, et. al.: J. Am. Chem. Soc., 120 (33), 8531-8532 (1998) (Non Patent Literature 2). A reaction formula is shown below.

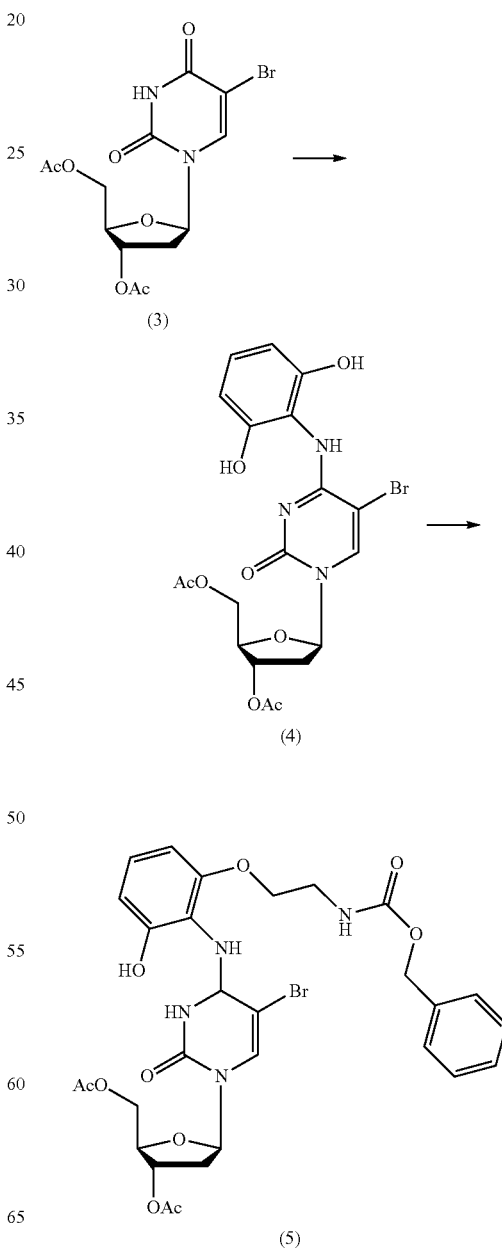

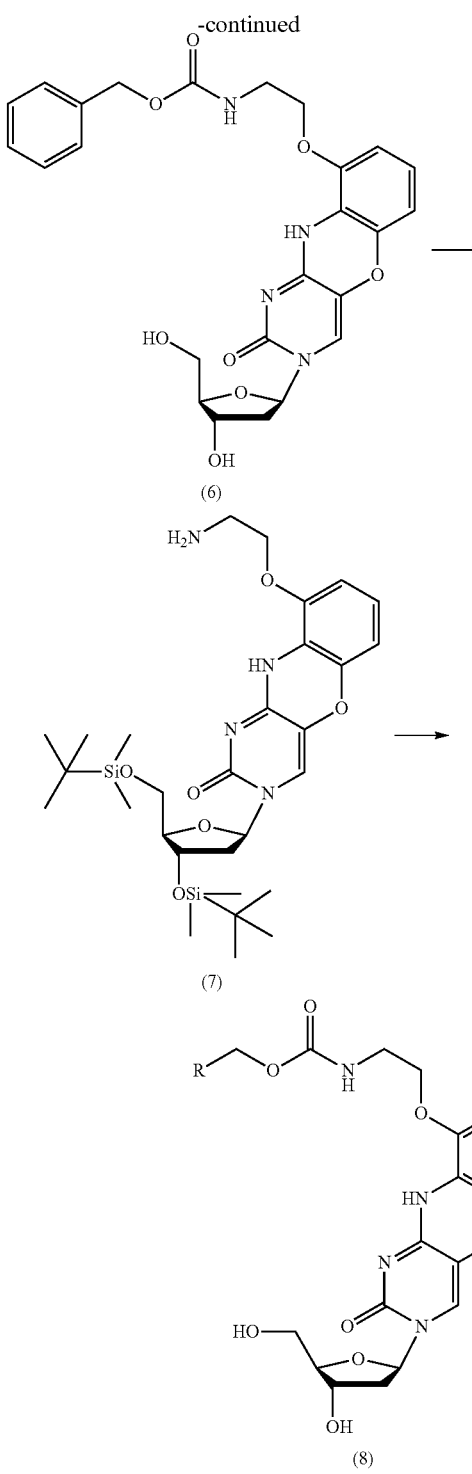

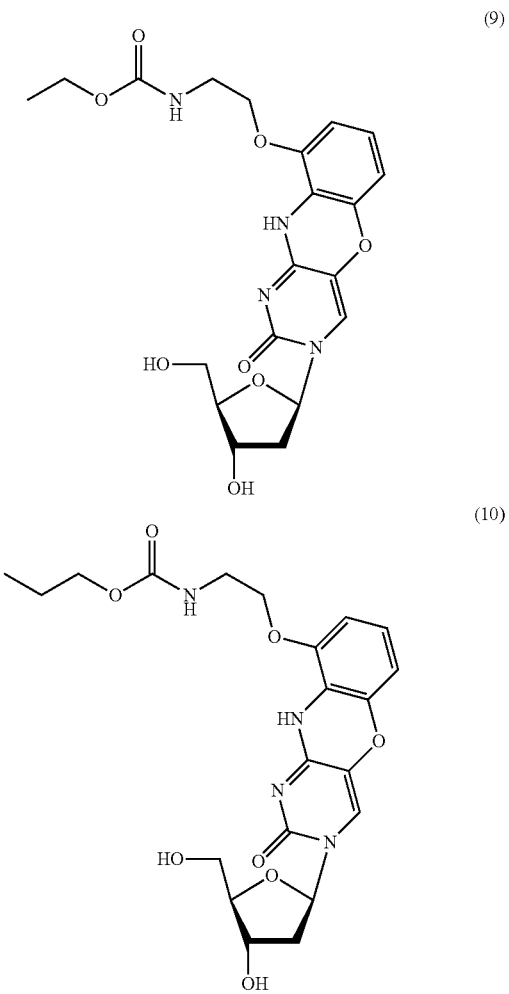

amino group thus produced is introduced into various carbamates. Thus, an intermediate (8) can be synthesized.

A known method may be used in the introduction of the phenoxazine compound into the polymer including the repeating units each represented by the formula (1). As an example, a compound in which the linking group L is an oxycarbonyl group may be synthesized by using a phenoxazine compound having a hydroxyl group and a polymer having a carboxyl group through a condensation reaction. At the time of the reaction, 1-(3-dimethylaminopropyl)-3-ethylcarbodiimide hydrochloride or the like may be used.

Alternatively, for example, a compound in which the linking group L is a carbonyloxy group may be synthesized by using a phenoxazine compound having a carboxyl group and a polymer having a hydroxyl group, a compound in which the linking group L is a carbonylamino group may be synthesized by using the phenoxazine compound having a carboxyl group and a polymer having an amino group, and a compound in which the linking group L is an aminocarbonyl group may be synthesized by using a phenoxazine compound having an amino group and the polymer having a carboxyl group.

Phenoxazine compounds (9) to (25) and the intermediate (6) are shown below as specific examples of the phenoxazine compound to be used in the synthesis of the compound according to the embodiment of the present invention. However, the present invention is not limited thereto.

5-Bromo-2'-deoxyuridine diacetate (3) is used as a starting material, and is caused to react with 2-aminoresorcinol to provide a compound (4). The compound and 2-(carbobenzoxyamino)-1-ethanol are caused to react with each other to provide a compound (5). Ammonia is caused to act on the compound to perform its cyclization, and at the same time, the deprotection of acetyl groups. Thus, an intermediate (6) can be synthesized. A compound (7) is obtained by: protecting hydroxyl groups with silyl groups; and deprotecting a benzyloxycarbonyl group through hydrogenation. An

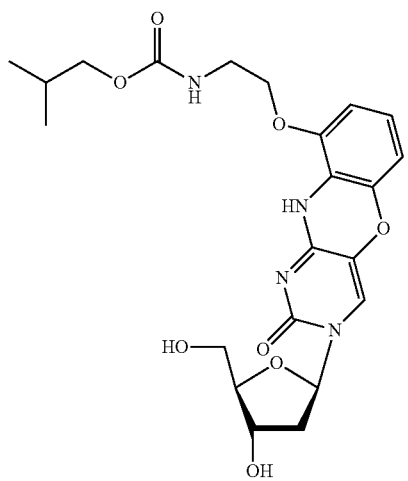
(11)
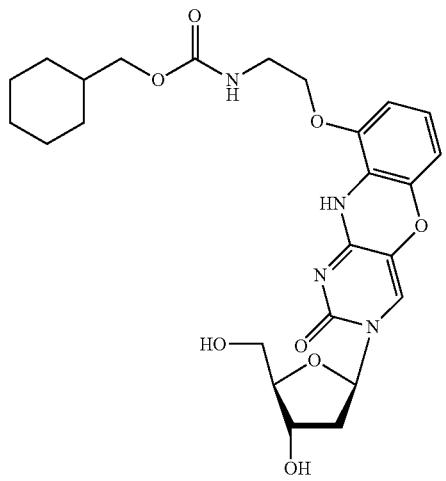
(14)
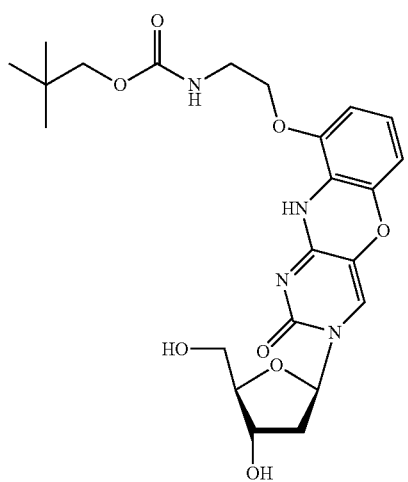
(12)
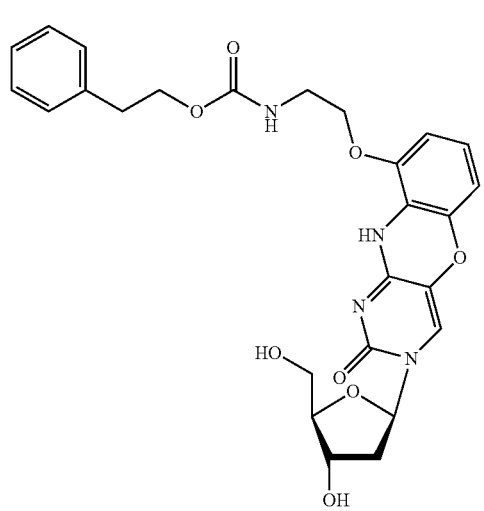
(15)
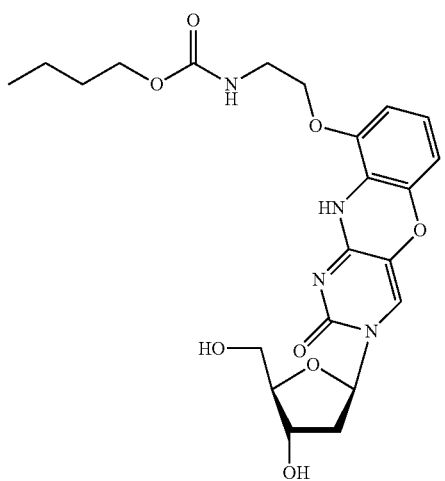
(13)
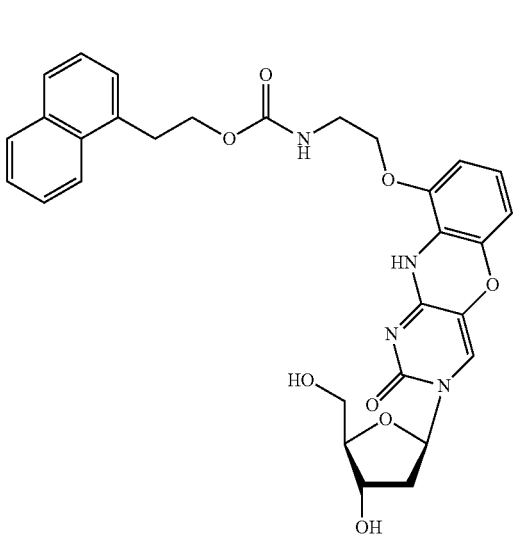
(16)

17
-continued
(17)
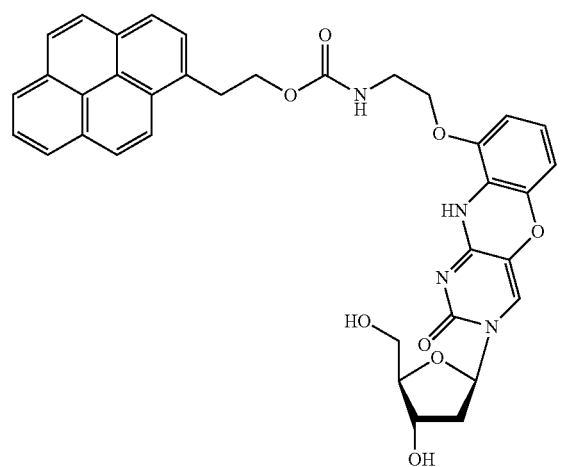
(6)
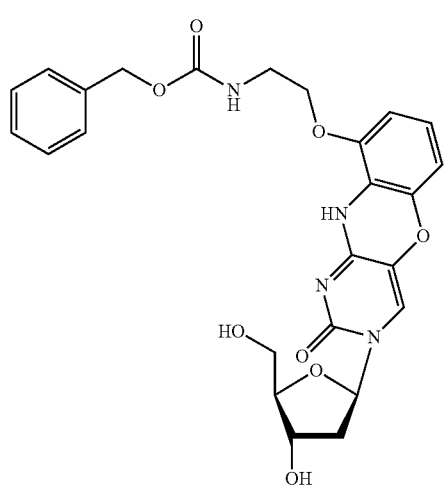
(18)
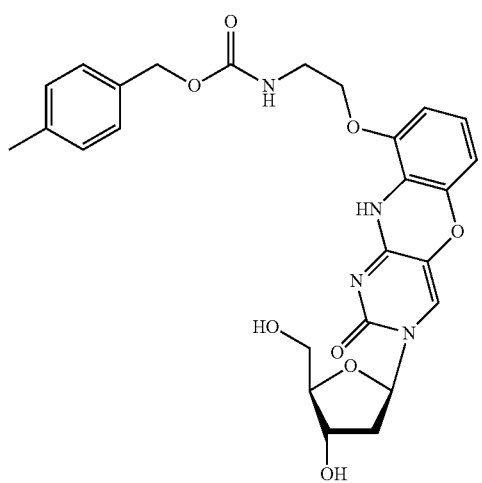
18
-continued
(19)
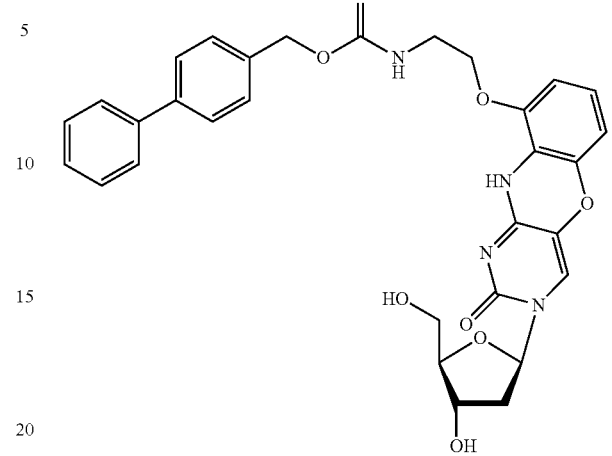
(20)
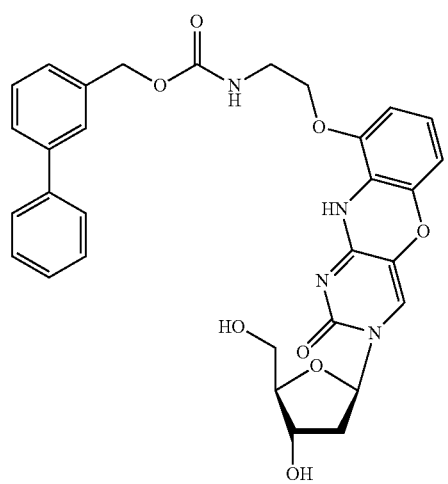
(21)
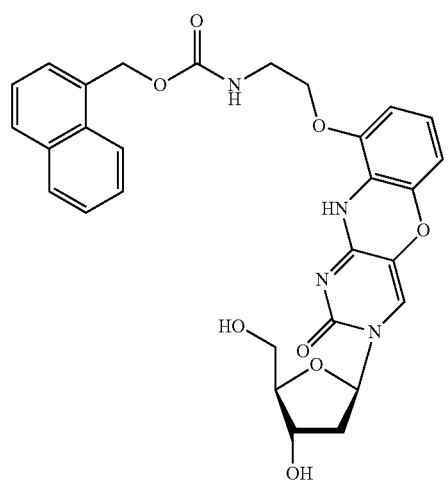

(22)
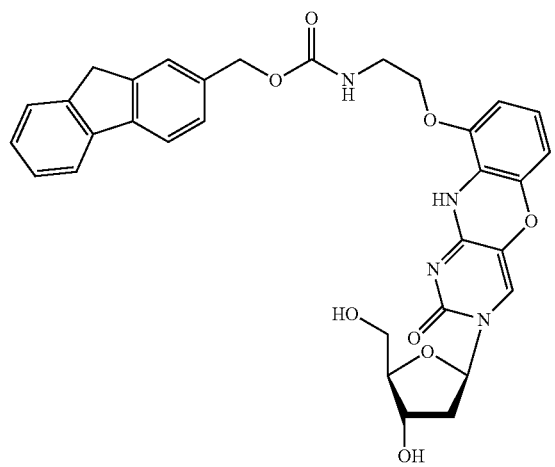

(23)
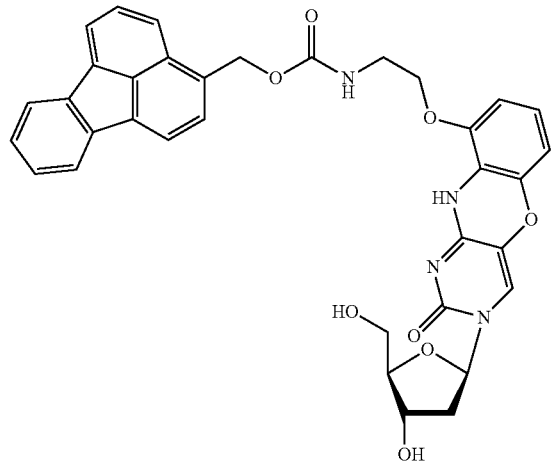

(24)
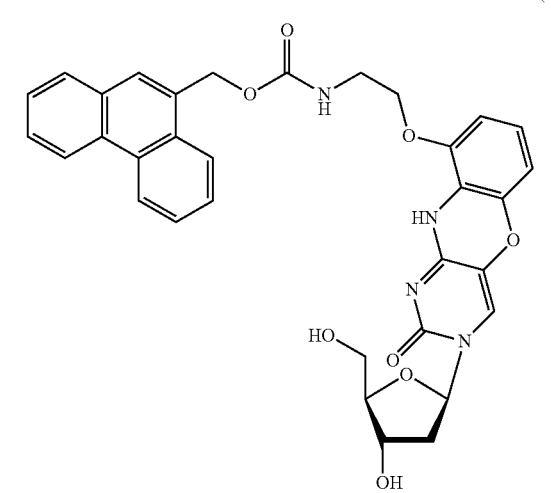

(25)
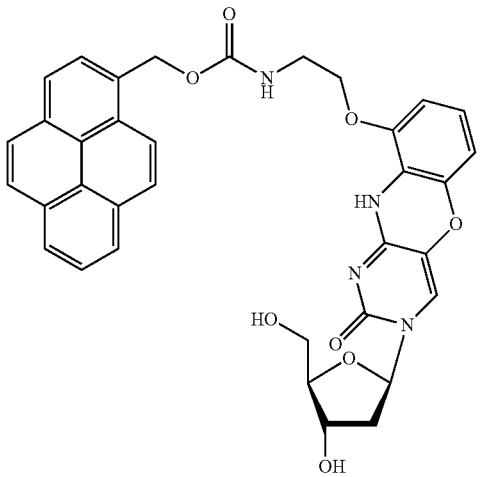

Now, the present invention is more specifically described by way of Examples. The present invention is not limited to these Examples, and various modifications may be made without departing from the gist of the present invention.

Synthesis Example 1

<Synthesis of Polymer 1>

A polyacrylic acid (manufactured by Wako Pure Chemical Industries, Ltd.) and the phenoxazine compound (9) were prepared at a molar ratio of 1:1, and were mixed in chloroform. After that, 1-(3-dimethylaminopropyl)-3-ethylcarbodiimide hydrochloride was added as a condensing agent to the mixture, and the whole was stirred overnight. After the completion of the reaction, the resultant was washed with water and filtered under reduced pressure, followed by vacuum drying. Thus, a target polymer 1 was obtained.

<Synthesis of Polymer 2>

A target polymer is obtained by the same method as that of the synthesis example of the polymer 1 except that the phenoxazine compound (9) is changed to the phenoxazine compound (12).

<Synthesis of Polymer 3>

A target polymer is obtained by the same method as that of the synthesis example of the polymer 1 except that the phenoxazine compound (9) is changed to the phenoxazine compound (14).

<Synthesis of Polymer 4>

A target polymer was obtained by the same method as that of the synthesis example of the polymer 1 except that the phenoxazine compound (9) was changed to the phenoxazine compound (15).

<Synthesis of Polymer 5>

A target polymer is obtained by the same method as that of the synthesis example of the polymer 1 except that the phenoxazine compound (9) is changed to the phenoxazine compound (16).

<Synthesis of Polymer 6>

A target polymer is obtained by the same method as that of the synthesis example of the polymer 1 except that the phenoxazine compound (9) is changed to the phenoxazine compound (17).

<Synthesis of Polymer 7>

A target polymer was obtained by the same method as that of the synthesis example of the polymer 1 except that the phenoxazine compound (9) was changed to the phenoxazine compound (6).

<Synthesis of Polymer 8>
A target polymer is obtained by the same method as that of the synthesis example of the polymer 1 except that the phenoxazine compound (9) is changed to the phenoxazine compound (19).

<Synthesis of Polymer 9>
A target polymer is obtained by the same method as that of the synthesis example of the polymer 1 except that the phenoxazine compound (9) is changed to the phenoxazine compound (22).

<Synthesis of Polymer 10>
A target polymer is obtained by the same method as that of the synthesis example of the polymer 1 except that the phenoxazine compound (9) is changed to the phenoxazine compound (23).

<Synthesis of Polymer 11>
A target polymer was obtained by the same method as that of the synthesis example of the polymer 1 except that the polyacrylic acid was changed to the JONCRYL 683 (manufactured by BASF).

<Synthesis of Polymer 12>
A target polymer is obtained by the same method as that of the synthesis example of the polymer 11 except that the phenoxazine compound (9) is changed to the phenoxazine compound (11).

<Synthesis of Polymer 13>
A target polymer is obtained by the same method as that of the synthesis example of the polymer 11 except that the phenoxazine compound (9) is changed to the phenoxazine compound (15).

<Synthesis of Polymer 14>
A target polymer is obtained by the same method as that of the synthesis example of the polymer 11 except that the phenoxazine compound (9) is changed to the phenoxazine compound (17).

<Synthesis of Polymer 15>
A target polymer was obtained by the same method as that of the synthesis example of the polymer 11 except that the phenoxazine compound (9) was changed to the phenoxazine compound (6).

<Synthesis of Polymer 16>
A target polymer was obtained by the same method as that of the synthesis example of the polymer 11 except that the molar ratio between the JONCRYL 683 and the phenoxazine compound (9) was changed to 1:2.

<Synthesis of Polymer 17>
A target polymer was obtained by the same method as that of the synthesis example of the polymer 11 except that the molar ratio between the JONCRYL 683 and the phenoxazine compound (9) was changed to 1:5.

<Synthesis of Polymer 18>
A target polymer was obtained by the same method as that of the synthesis example of the polymer 11 except that the molar ratio between the JONCRYL 683 and the phenoxazine compound (9) was changed to 1:10.

<Synthesis of Polymer 19>
A target polymer is obtained by the same method as that of the synthesis example of the polymer 11 except that the phenoxazine compound (9) is changed to the phenoxazine compound (19).

<Synthesis of Polymer 20>
A target polymer is obtained by the same method as that of the synthesis example of the polymer 11 except that the phenoxazine compound (9) is changed to the phenoxazine compound (22).

<Synthesis of Polymer 21>
A target polymer is obtained by the same method as that of the synthesis example of the polymer 11 except that the phenoxazine compound (9) is changed to the phenoxazine compound (23).

Here, a method of calculating an 8-OHdG adsorption ratio in Examples of the present invention is described by taking the polymer 7 as an example. A spectrofluorophotometer F-4500 (manufactured by Hitachi High-Technologies Corporation) was used in the following fluorescence measurement.

The polymer 7 (2 mg) was dissolved in 3 ml of chloroform, and the wavelength of UV absorbed by the solution was measured, followed by the calculation of the concentration of a phenoxazine derivative from the resultant value. A chloroform solution having a phenoxazine derivative concentration of 30 μM was prepared, and its fluorescence was measured ($FL_f$). One equivalent of a 3 mM solution of 8-OHdG in chloroform (containing 10% dimethyl sulfoxide) was added to the solution, and the fluorescence of the mixture was measured ($FL_O$). $1-FL_O/FL_f$ was calculated and defined as an adsorption ratio.

In Examples of the present invention, the evaluation of the adsorption ratio was performed based on the following criteria. Levels A to C were defined as acceptable levels, and a level D was defined as an unacceptable level.
A: Adsorption ratio of 0.90 or more
B: Adsorption ratio of 0.75 or more and less than 0.90
C: Adsorption ratio of 0.50 or more and less than 0.75
D: Adsorption ratio of less than 0.50

The results of the evaluations of the adsorption ratios of the polymers obtained in Examples of the present invention are shown in Table 1.

TABLE 1

| Example | Name | Adsorption ratio |
| --- | --- | --- |
| Example 1 | Polymer 1 | B |
| Example 2 | Polymer 2 | C |
| Example 3 | Polymer 3 | — |
| Example 4 | Polymer 4 | A |
| Example 5 | Polymer 5 | — |
| Example 6 | Polymer 6 | — |
| Example 7 | Polymer 7 | A |
| Example 8 | Polymer 8 | — |
| Example 9 | Polymer 9 | — |
| Example 10 | Polymer 10 | — |
| Example 11 | Polymer 11 | B |
| Example 12 | Polymer 12 | — |
| Example 13 | Polymer 13 | — |
| Example 14 | Polymer 14 | — |
| Example 15 | Polymer 15 | A |
| Example 16 | Polymer 16 | A |
| Example 17 | Polymer 17 | A |
| Example 18 | Polymer 18 | A |
| Example 19 | Polymer 19 | — |
| Example 20 | Polymer 20 | — |
| Example 21 | Polymer 21 | — |
| Comparative Example | Intermediate 6 | A |

Here, the reuse of a polymer is described by taking, as examples, the polymer 15 and the intermediate (6) serving as a comparative example. The polymer 15 used in the evaluation was washed with methanol, and then its adsorption ratio was measured again. The same operation was performed on the intermediate (6), and its adsorption ratio was measured. Results obtained by performing each operation five times are shown in Table 2. Unlike the comparative example, in Example 22, the adsorption ratio did not reduce even in the fifth adsorption.

TABLE 2

| Example | Name | Adsorption ratio (first) | Adsorption ratio (fifth) |
|---|---|---|---|
| Example 22 | Polymer 15 | A | A |
| Comparative Example 2 | Intermediate 6 | A | D |

In Examples of the present invention, the polymers 15 to 18 each having introduced thereinto a plurality of phenoxazine compounds each represented by the formula (2) were used in amounts identical to each other, and the 8-OHdG solution was added in an amount of from 0 equivalents to 10 equivalents to each of the polymers. The adsorption ratios of the resultant mixtures were measured, and their changes with time were observed. As compared to the polymer 15, such an amount of the solution that the fluorescence intensity of each of the other polymers was saturated was proportional to the amount of the introduced phenoxazine compounds.

It was shown from the foregoing that the polymer of the present invention was able to be used in the detection and measuring of 8-oxo-2'-deoxyguanosine, and was repeatedly used by being washed.

The polymer in the present invention can perform specific sensing of an oxidative stress in a living organism at relatively low cost with relative ease through the detection of 8-oxo-2'-deoxyguanosine. Further, the polymer can be reused by a simple treatment even after its use.

According to the present invention, there is provided a novel polymer having introduced thereinto a phenoxazine compound. The polymer having introduced thereinto the phenoxazine compound of the present invention has a high affinity for 8-OHdG and satisfactorily acts as an 8-OHdG-detecting agent that can be repeatedly used.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2017-083067, filed Apr. 19, 2017, which is hereby incorporated by reference herein in its entirety.

What is claimed is:

1. A polymer, comprising 30 to 100 repeating units, each represented by formula (1):

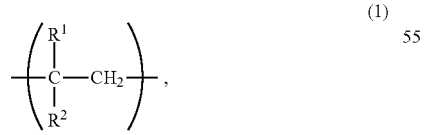

where, in the formula (1), $R^1$ and $R^2$ are each independent for each repeating unit, $R^1$ represents a hydrogen atom or an alkyl group, and $R^2$ represents a group represented by formula (2) in at least one repeating unit, and represents a phenyl group, a hydroxyl group, an amino group, or a carboxyl group in any other repeating unit, and the group may be substituted with an alkyl group:

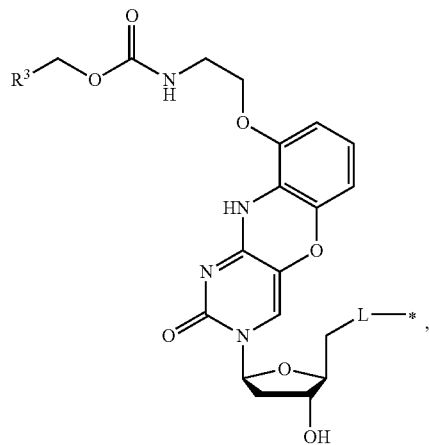

where, in the formula (2), $R^3$ represents a hydrogen atom, an alkyl group, or an aryl group, L represents a divalent linking group, and * represents a site to be bonded to the carbon atom bonding to $R^1$ in the formula (1).

2. The polymer according to claim 1, wherein L in the formula (2) represents an oxycarbonyl group (—O—CO—), a carbonyloxy group (—CO—O—), a carbonylamino group (—CO—NH—), or an aminocarbonyl group (—NH—CO—), or a group further including an alkylene group at one terminal, or each of both terminals, of any one of the groups.

3. The polymer according to claim 1 or 2, wherein $R^3$ represents a phenyl group.

4. A method of detecting 8 oxo-2'-deoxyguanosine, which comprises utilizing the polymer according to claim 1.

5. The polymer according to claim 1, wherein the polymer comprises 40 to 60 repeating units each represented by the formula (1).

6. The polymer according to claim 1, wherein the polymer comprises 5 to 10 repeating units each represented by the formula (1) in which $R^2$ represents a group represented by the formula (2).

7. A polymer, comprising 30 to 100 repeating units represented by formula (26):

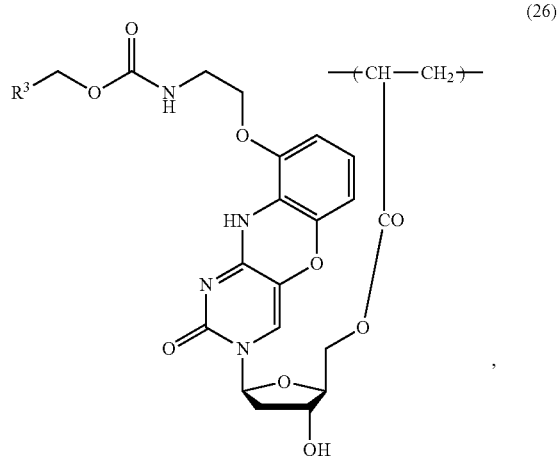

where, in the formula (26), $R^3$ represents a hydrogen atom, an alkyl group, or an aryl group.

8. The polymer according to claim 7, further comprising a repeating unit represented by formula (27):

where, in the formula (27), X represents a counter ion.
* * * * *